United States Patent
Bhagat et al.

(10) Patent No.: US 9,585,911 B2
(45) Date of Patent: Mar. 7, 2017

(54) SACHET FORMULATION FOR AMINE POLYMERS

(71) Applicant: Genzyme Corporation, Cambridge, MA (US)

(72) Inventors: Hitesh R. Bhagat, Wayland, MA (US); Jeffrey M. Goldberg, Framingham, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 14/750,459

(22) Filed: Jun. 25, 2015

(65) Prior Publication Data

US 2016/0113961 A1 Apr. 28, 2016

Related U.S. Application Data

(62) Division of application No. 11/519,982, filed on Sep. 12, 2006, now Pat. No. 9,095,509.

(60) Provisional application No. 60/717,200, filed on Sep. 15, 2005.

(51) Int. Cl.

| | |
|---|---|
| A61K 9/14 | (2006.01) |
| A61K 31/787 | (2006.01) |
| A61K 9/00 | (2006.01) |
| A61K 31/00 | (2006.01) |
| A61K 31/785 | (2006.01) |
| A61K 9/16 | (2006.01) |
| A61K 8/81 | (2006.01) |
| A61K 8/898 | (2006.01) |
| A61K 47/34 | (2006.01) |
| A61K 47/36 | (2006.01) |

(52) U.S. Cl.
CPC .......... *A61K 31/787* (2013.01); *A61K 9/0053* (2013.01); *A61K 9/0056* (2013.01); *A61K 9/0095* (2013.01); *A61K 9/1652* (2013.01); *A61K 31/00* (2013.01); *A61K 31/785* (2013.01); *A61K 8/8105* (2013.01); *A61K 8/817* (2013.01); *A61K 8/898* (2013.01); *A61K 47/34* (2013.01); *A61K 47/36* (2013.01)

(58) Field of Classification Search
None
See application file for complete search history.

(56) References Cited

U.S. PATENT DOCUMENTS

| | | |
|---|---|---|
| 2,426,125 A | 8/1947 | Steiner |
| 2,456,428 A | 12/1948 | Parker |
| 2,463,824 A | 3/1949 | Steiner et al. |
| 3,104,205 A | 9/1963 | Hainer et al. |
| 3,308,020 A | 3/1967 | Tennant et al. |
| 3,332,841 A | 7/1967 | Ainsworth et al. |
| 3,383,236 A | 5/1968 | Brindamour |
| 3,431,138 A | 3/1969 | Zingerman et al. |
| 3,539,380 A | 11/1970 | Johnson et al. |
| 3,624,209 A | 11/1971 | Granatek et al. |
| 3,980,770 A | 9/1976 | Ingelman et al. |
| 4,016,209 A | 4/1977 | Wagner et al. |
| 4,071,478 A | 1/1978 | Shen et al. |
| 4,115,537 A | 9/1978 | Driscoll et al. |
| 4,143,130 A | 3/1979 | Imondi et al. |
| 4,172,120 A | 10/1979 | Todd et al. |
| 4,181,718 A | 1/1980 | Mason et al. |
| 4,183,918 A | 1/1980 | Asher et al. |
| 4,205,064 A | 5/1980 | Wagner et al. |
| 4,211,763 A | 7/1980 | Marshall et al. |
| 4,247,393 A | 1/1981 | Wallace |
| 4,264,573 A | 4/1981 | Powell et al. |
| 4,302,440 A | 11/1981 | John et al. |
| 4,341,563 A | 7/1982 | Kurihara et al. |
| 4,344,993 A | 8/1982 | Schmidt et al. |
| 4,439,419 A | 3/1984 | Vecchio |
| 4,504,640 A | 3/1985 | Harada et al. |
| 4,507,466 A | 3/1985 | Tomalia et al. |
| 4,518,433 A | 5/1985 | McGinley et al. |
| 4,528,184 A | 7/1985 | Kurono et al. |
| 4,539,198 A | 9/1985 | Powell et al. |
| 4,543,370 A | 9/1985 | Porter et al. |
| 4,605,701 A | 8/1986 | Harada et al. |
| 4,631,305 A | 12/1986 | Guyer et al. |
| 4,762,524 A | 8/1988 | Chambers et al. |
| 4,849,227 A | 7/1989 | Cho |
| 4,853,437 A | 8/1989 | Lukach et al. |
| 4,871,779 A | 10/1989 | Killat et al. |
| 4,895,621 A | 1/1990 | Hassler |
| 4,956,182 A | 9/1990 | Bequette et al. |

(Continued)

FOREIGN PATENT DOCUMENTS

| | | |
|---|---|---|
| CH | 656 535 A5 | 7/1986 |
| DE | 4010271 | 10/1991 |

(Continued)

OTHER PUBLICATIONS

Bhadra, D. et al., "Glycodendrimeric Nanoparticulate Carriers of Primaquine Phosphate for Liver Targeting" International Journal of Pharmaceutics, 295 (Mar. 2005) 221-233.

Caramella, Carla et al. "Experimental Evidence of Disintegration Mechanisms" Acta Pharm. Technol., 35:1 (1989) 30-33.

Chertow, Glenn M. et al. "The Effects of Sevelamer and Calcium Acetate on Proxies of Atherosclerotic and Arteriosclerotic Vascular Disease in Hemodialysis Patients" Am. J. Nephrol., 23:5 (2003) 307-314.

De Brabander-Van Den Berg, Ellen M. M. et al., "Poly(propylenimin)-Dendrimere: Synthese in größerem Maßstab durch heterogen katalysierte Hydrierungen" Angew. Chem. (1993) 1370-1372. [in German only].

(Continued)

Primary Examiner — James Rogers
(74) Attorney, Agent, or Firm — Jones Day

(57) ABSTRACT

A powder formulation comprises a pharmaceutically acceptable anionic stabilizer and an aliphatic amine polymer or a pharmaceutically acceptable salt thereof mixed with the anionic stabilizer. The powder formulation is conveniently packaged in a container, such as a sachet. A method of treating a subject with hyperphosphotemia with the powder formulation is also disclosed.

21 Claims, No Drawings

(56) References Cited

U.S. PATENT DOCUMENTS

| | | |
|---|---|---|
| 4,983,398 A | 1/1991 | Gaylord et al. |
| 4,983,399 A | 1/1991 | Maish |
| 5,053,423 A | 10/1991 | Liu |
| 5,055,197 A | 10/1991 | Albright et al. |
| 5,073,380 A | 12/1991 | Babu et al. |
| 5,108,767 A | 4/1992 | Mulchandani et al. |
| 5,194,464 A | 3/1993 | Itoh et al. |
| 5,262,167 A | 11/1993 | Vegesna et al. |
| 5,302,531 A | 4/1994 | Bauer |
| 5,373,052 A | 12/1994 | Fukuda et al. |
| 5,374,422 A | 12/1994 | St. Pierre et al. |
| 5,376,396 A | 12/1994 | Clark |
| 5,401,515 A | 3/1995 | Woodard et al. |
| 5,414,068 A | 5/1995 | Bliem et al. |
| 5,428,112 A | 6/1995 | Ahlers et al. |
| 5,430,110 A | 7/1995 | Ahlers et al. |
| 5,447,726 A | 9/1995 | Nomura |
| 5,455,047 A | 10/1995 | Bequette et al. |
| 5,462,730 A | 10/1995 | McTaggart et al. |
| 5,487,888 A | 1/1996 | Mandeville et al. |
| 5,496,545 A | 3/1996 | Holmes-Farley et al. |
| 5,520,932 A | 5/1996 | McCurdy et al. |
| 5,530,092 A | 6/1996 | Meijer et al. |
| 5,561,214 A | 10/1996 | Yeske et al. |
| 5,607,669 A | 3/1997 | Mandeville, III et al. |
| 5,610,268 A | 3/1997 | Meijer et al. |
| 5,618,530 A | 4/1997 | Mandeville, III et al. |
| 5,624,963 A | 4/1997 | Mandeville, III et al. |
| 5,654,003 A | 8/1997 | Fuisz et al. |
| 5,667,775 A | 9/1997 | Holmes-Farley et al. |
| 5,679,717 A | 10/1997 | Mandeville, III et al. |
| 5,686,106 A | 11/1997 | Kelm et al. |
| 5,693,675 A | 12/1997 | Mandeville, III et al. |
| 5,702,696 A | 12/1997 | Mandeville, III et al. |
| 5,703,188 A | 12/1997 | Mandeville, III et al. |
| 5,709,880 A | 1/1998 | Del Corral et al. |
| 5,718,920 A | 2/1998 | Notenbomber |
| 5,747,067 A | 5/1998 | Auguello et al. |
| 5,750,148 A | 5/1998 | Maruyama et al. |
| 5,807,582 A | 9/1998 | Cha |
| 5,814,336 A | 9/1998 | Kelm et al. |
| 5,840,339 A | 11/1998 | Kunin |
| 5,840,766 A | 11/1998 | Mandeville, III et al. |
| 5,900,475 A | 5/1999 | Mandeville, III et al. |
| 5,919,832 A | 7/1999 | Mandeville, III et al. |
| 5,959,069 A | 9/1999 | Gluck et al. |
| 5,969,090 A | 10/1999 | Mandeville, III et al. |
| 5,985,938 A | 11/1999 | Holmes-Farley et al. |
| 6,022,533 A | 2/2000 | Goto et al. |
| 6,034,129 A | 3/2000 | Mandeville, III et al. |
| 6,037,444 A | 3/2000 | Rannard et al. |
| 6,083,495 A | 7/2000 | Holmes-Farley et al. |
| 6,083,497 A | 7/2000 | Huval et al. |
| 6,090,411 A | 7/2000 | Vineaa Pillay et al. |
| 6,149,938 A | 11/2000 | Bonadeao et al. |
| 6,177,478 B1 | 1/2001 | Holmes-Farley et al. |
| 6,180,754 B1 | 1/2001 | Stutts et al. |
| 6,187,897 B1 | 2/2001 | Kawashima et al. |
| 6,190,650 B1 | 2/2001 | Matthews et al. |
| 6,203,785 B1 | 3/2001 | Holmes-Farley et al. |
| 6,248,318 B1 | 6/2001 | Huval et al. |
| 6,264,937 B1 | 7/2001 | Mandeville, III et al. |
| 6,274,713 B1 | 8/2001 | Sieving et al. |
| 6,281,252 B1 | 8/2001 | Holmes-Farley et al. |
| 6,284,275 B1 | 9/2001 | Chen |
| 6,335,402 B1 | 1/2002 | Mihan et al. |
| 6,362,266 B1 | 3/2002 | Buchholz et al. |
| 6,383,518 B1 | 5/2002 | Matsuda et al. |
| 6,423,754 B1 | 7/2002 | Holmes-Farley et al. |
| 6,509,013 B1 | 1/2003 | Holmes-Farley et al. |
| 6,534,600 B2 | 3/2003 | Dvornic et al. |
| 6,566,407 B2 | 5/2003 | Holmes-Farley et al. |
| 6,600,011 B2 | 7/2003 | McDonnell et al. |
| 6,605,270 B1 | 8/2003 | Mandeville et al. |
| 6,696,087 B2 | 2/2004 | Matsuda et al. |
| 6,726,905 B1 | 4/2004 | Mandeville, III et al. |
| 6,733,780 B1 | 5/2004 | Tyler et al. |
| 6,844,372 B2 | 1/2005 | Goto et al. |
| 6,858,203 B2 | 2/2005 | Holmes-Farley et al. |
| 6,908,609 B2 | 6/2005 | Simon et al. |
| 7,014,846 B2 | 3/2006 | Holmes-Farley et al. |
| 7,019,085 B2 | 3/2006 | Albright |
| 7,081,509 B2 | 7/2006 | Wagner et al. |
| 7,087,223 B2 | 8/2006 | Goto et al. |
| 7,101,960 B2 | 9/2006 | Mandeville, III et al. |
| 7,220,406 B2 | 5/2007 | Burke |
| 7,335,795 B2 | 2/2008 | Chang et al. |
| 7,342,083 B2 | 3/2008 | Chang et al. |
| 7,385,012 B2 | 6/2008 | Chang et al. |
| 7,449,605 B2 | 11/2008 | Chang et al. |
| 7,459,151 B2 | 12/2008 | Holmes-Farley et al. |
| 7,459,502 B2 | 12/2008 | Connor et al. |
| 7,589,238 B2 | 9/2009 | Connor et al. |
| 7,638,524 B2 | 12/2009 | Huval et al. |
| 7,985,418 B2 | 7/2011 | Bhagat et al. |
| 9,095,509 B2 | 8/2015 | Bhagat et al. |
| 2002/0054903 A1 | 5/2002 | Tyler et al. |
| 2002/114774 A1 | 8/2002 | Fitzpatrick et al. |
| 2002/0122786 A1 | 9/2002 | Matsuda et al. |
| 2002/0159968 A1 | 10/2002 | Petersen et al. |
| 2002/0160050 A1 | 10/2002 | Elema et al. |
| 2002/0168333 A1 | 11/2002 | Burke |
| 2002/0182168 A1 | 12/2002 | Holmes-Farley et al. |
| 2002/0187120 A1 | 12/2002 | Holmes-Farley et al. |
| 2002/0187121 A1 | 12/2002 | Burke |
| 2003/0003113 A1 | 1/2003 | Lewandowski |
| 2003/0039627 A1 | 2/2003 | Holmes-Farley et al. |
| 2003/0049226 A1 | 3/2003 | Burke et al. |
| 2003/0086898 A1 | 5/2003 | Holmes-Farley et al. |
| 2003/0133902 A1 | 7/2003 | Holmes-Farley et al. |
| 2003/0161875 A1 | 8/2003 | Murpani et al. |
| 2003/0175349 A1 | 9/2003 | Garg et al. |
| 2003/0180250 A1 | 9/2003 | Chauhan et al. |
| 2003/0199090 A1 | 10/2003 | Monahan et al. |
| 2003/0215585 A1 | 11/2003 | Bunick |
| 2004/0019020 A1 | 1/2004 | Jozefiak et al. |
| 2004/0022844 A1 | 2/2004 | Hasenzahl et al. |
| 2004/0120922 A1 | 6/2004 | Burke |
| 2004/0166156 A1 | 8/2004 | Tyler et al. |
| 2004/0170695 A1 | 9/2004 | Elama et al. |
| 2004/0185111 A1 | 9/2004 | Rubino et al. |
| 2004/0191209 A1 | 9/2004 | Oba |
| 2004/0191212 A1 | 9/2004 | Holmes-Farley et al. |
| 2005/0084476 A1 | 4/2005 | Goto et al. |
| 2005/0096438 A1 | 5/2005 | Chang et al. |
| 2005/0123614 A1 | 6/2005 | Kim et al. |
| 2005/0131138 A1 | 6/2005 | Connor et al. |
| 2005/0131161 A1 | 6/2005 | Mandeville, III et al. |
| 2005/0147580 A1 | 7/2005 | Connor et al. |
| 2005/0165190 A1 | 7/2005 | Chang et al. |
| 2005/0208095 A1 | 9/2005 | Hunter et al. |
| 2005/0209423 A1 | 9/2005 | Chang et al. |
| 2005/0220752 A1 | 10/2005 | Charmot et al. |
| 2005/0220889 A1 | 10/2005 | Charmot et al. |
| 2005/0220890 A1 | 10/2005 | Charmot et al. |
| 2005/0239901 A1 | 10/2005 | Chang et al. |
| 2005/0260236 A1 | 11/2005 | Tyler et al. |
| 2005/0282010 A1 | 12/2005 | Xu |
| 2006/0024336 A1 | 2/2006 | Charmot et al. |
| 2006/0024368 A1 | 2/2006 | Fassihi et al. |
| 2006/0029663 A1 | 2/2006 | Uchida et al. |
| 2006/0034914 A1 | 2/2006 | Tyler et al. |
| 2006/0043984 A1 | 3/2006 | Miller et al. |
| 2006/0047086 A1 | 3/2006 | Albright et al. |
| 2006/0054914 A1 | 3/2006 | Hsian Yi |
| 2006/0088592 A1 | 4/2006 | Choi et al. |
| 2006/0116391 A1 | 6/2006 | Horbury et al. |
| 2006/0134225 A1 | 6/2006 | Moerck et al. |
| 2006/0171916 A1 | 8/2006 | Holmes-Farley et al. |
| 2006/0177415 A1 | 8/2006 | Burke |
| 2006/0239959 A1 | 10/2006 | Holmes-Farley et al. |
| 2006/0251614 A1 | 11/2006 | Bhagat et al. |
| 2006/0258812 A1 | 11/2006 | Gopalkrishna et al. |
| 2006/0292192 A1 | 12/2006 | Hasenzahl et al. |

(56) References Cited

U.S. PATENT DOCUMENTS

| | | |
|---|---|---|
| 2007/0035313 A1 | 2/2007 | Wuersch et al. |
| 2007/0059277 A1 | 3/2007 | Bhagat et al. |
| 2007/0071715 A1 | 3/2007 | DeLuca et al. |
| 2007/0094779 A1 | 5/2007 | Dauphin |
| 2007/0098678 A1 | 5/2007 | Bhagat et al. |
| 2007/0110707 A1 | 5/2007 | Ravi |
| 2007/0155950 A1 | 7/2007 | Mandeville, III et al. |
| 2007/0190135 A1 | 8/2007 | Matsuda et al. |
| 2007/0224283 A1 | 9/2007 | Chang et al. |
| 2008/0014288 A1 | 1/2008 | Huval et al. |
| 2008/0107737 A1 | 5/2008 | Chang et al. |
| 2008/0226735 A1 | 9/2008 | Moerck et al. |
| 2008/0292697 A1 | 11/2008 | Tyler et al. |
| 2008/0299199 A1 | 12/2008 | Bar-Shalom et al. |

FOREIGN PATENT DOCUMENTS

| | | |
|---|---|---|
| EP | 0162388 | 11/1985 |
| EP | 0375350 | 6/1990 |
| EP | 0379161 | 7/1990 |
| EP | 0449151 | 10/1991 |
| EP | 0534304 | 3/1993 |
| EP | 0605757 | 7/1994 |
| EP | 0737759 | 10/1996 |
| EP | 0997148 | 5/2000 |
| EP | 1153940 | 11/2001 |
| EP | 1210935 | 6/2002 |
| EP | 1304104 | 4/2003 |
| EP | 0211991 | 3/2007 |
| FR | 2217010 | 9/1974 |
| FR | 2232563 | 1/1975 |
| GB | 929391 | 6/1963 |
| GB | 1238597 | 7/1971 |
| GB | 1470538 | 4/1977 |
| GB | 2036048 | 11/1978 |
| GB | 2391730 | 12/1978 |
| GB | 1573487 | 8/1980 |
| GB | 2090605 | 7/1982 |
| GB | 2276170 | 9/1994 |
| GB | 2169356 | 7/2000 |
| JP | 60152424 A | 8/1985 |
| JP | 62-132830 | 6/1987 |
| JP | 5-244915 | 9/1993 |
| JP | 6-321786 | 11/1994 |
| JP | 10-330269 | 12/1998 |
| JP | 10316576 A | 12/1998 |
| JP | 2000178182 A | 6/2000 |
| JP | 2006-008637 | 1/2006 |
| SU | 1808015 | 4/1993 |
| WO | WO 90/02148 | 3/1990 |
| WO | WO 92/10522 | 6/1992 |
| WO | WO 93/00915 | 1/1993 |
| WO | WO 93/05793 | 1/1993 |
| WO | WO 94/19379 | 1/1994 |
| WO | WO 94/04596 | 3/1994 |
| WO | WO 94/27620 | 12/1994 |
| WO | WO 94/27621 | 12/1994 |
| WO | WO 95/05184 | 2/1995 |
| WO | WO 96/21454 | 7/1996 |
| WO | WO 96/25440 | 8/1996 |
| WO | WO 97/49771 | 12/1997 |
| WO | WO 98/42355 | 10/1998 |
| WO | WO 99/22721 | 5/1999 |
| WO | WO 02/085378 | 10/2002 |
| WO | WO 2004/099288 | 11/2004 |
| WO | WO 2005/021000 | 3/2005 |
| WO | WO 2005/041902 | 5/2005 |
| WO | WO 2005/065291 | 7/2005 |
| WO | WO 2005/072752 | 8/2005 |
| WO | WO 2006/022759 | 3/2006 |
| WO | WO 2006/050314 | 5/2006 |
| WO | WO 2006/050315 | 5/2006 |
| WO | WO 2007/035313 | 3/2007 |

OTHER PUBLICATIONS

Duncan, Ruth et al., "Dendrimer biocompatibility and toxicity" Advanced Drug Delivery Reviews, 57 (2005) 2215-2237.

Ferrari, F. et al. "Investigation on Bonding and Distintegration Properties of Pharmaceutical Materials" International Journal of Pharmaceutics, 136 (1996) 71-79.

Gao, C., "Hyperbranched polymers made from A2, B2 and BB'2 type monomers, 2. Preparation of hyperbranched copoly(sulfone-amine)s by polyaddition of N-ethylethylenediamine and piperazine to divinylsulfone" Polymer (2001), 42(8), 3437-3443.

Gao, C., "Preparation of Water Soluble hyperbranched poly(sulfone-amine)s by polyaddition of N-ethylethylenediamine to divinyl sulfone" Polymer (2001), 42(18), 7603-7610.

Gao, Chao, "Hyperbranched copolymers made from A2, B2 and BB'2 type monomers (iv). Copolymerization of divinyl sulfone with 4,4'-trimethylenedipiperidine and N-ethylethylenediamine" Science in China, Series B: Chemistry (2001), 44(2), 207-215.

Gao, Chao, "Hyperbranched copolymers made from A2, B2 and BB'2 type monomers, 3a: comparison of copoly(sulfone-amine)s containing piperazine and 4,4'-trimethylenedipiperidine units" Macromolecular Chemistry and Physics (2001), 202(15), 3035-3042.

Gao, Chao, "Hyperbranched polymers made from A2- and BB2'-type monomers; 3. Polyaddition of N-methyl 1,3-propanediamine to divinyl sulfone" Macromolecular Chemistry and Physics (2001), 202(12), 2623-2629.

Gao, Chao, "Polyaddition of B2 and BB'2 Type Monomers to A2 Type Monomer. 1. Synthesis of Highly Branched Copoly(sulfon-amine)s" Macromolecules (2001), 34(2), 156-161.

Gao, Chao, "Synthesis of hyperbranched polymers from commercially available A2 and BB'2 type monomers" Chemical Communications (Cambridge), 1 (2001) 107-108.

Hammouda, Y. et al. "The Use of Sodium Chloride as a Directly Compressible Filler in Therapeutic Tablets" Pharm. Ind., 37:5 (1975) 361-363.

Hobson Lois J., et al. "Poly(amidoamine) Hyperbranched Systems:Synthesis, Structure and Characterization" Polymer, 40 (1999) 1279-1297.

Huval, Chad C. et al., "Syntheses of hydrophobically modified cationic hydrogels by copolymerization of alkyl substituted diallylamine monomers and their use as bile acid sequestrants" European Polymer Journal, 40 (2004) 693-701.

Jansen, Johan F.G.A. et al. "The Dendritic Box: Shape-Selective Liberation of Encapsulated Guests" J. Am. Chem. Soc., 117 (1995) 4417-4418.

Janssen, H.M. et al, "The Synthesis and Characterization of Dendritic Molecules" Eindhoven University of Technology [No date available].

Jayamurugan, Govindasamy, et al., "Synthesis of Large Generation poly(propul ether imine) (PETIM) Dendrimers" Tetrahedron, 62 (2006) 9582-9588.

Katopodis, K. P. et al. "Effectiveness of Aluminum Hydroxide Timing Administration in Relation to Meals in Controlling Hyperphosphatemia in Dialysis Patients" The International Journal of Artificial Organs, 28:8 (2005) 803-807.

Klapper, Marcus et al., "Poly(methylene amine): A Polymer with the Maximum Possible Number of Amino Groups on a Polymer Backbone" Angew. Chem. Int. Ed., 42 (2003) 4687-4690 (XP002456407).

Koç, Fikret, et al. "Highly Regioselective Synthesis pf Amino-Functionalized Dendritic PolyGlycerols by a One Pot Hydroformylation/Reductive Amination Sequence" J. Org. Chem., 70 (2005) 2021-2025.

Kremer, Michael, et al., "Pore-Size Distributions of Cationic Polyacrylamide Hydrogels Varying in Initial Monomer Concentration and Crosslnker/Monomer Ratio" Macromolecules, 27 (1994) 2965-2973.

Kuga, Shigenori, "Pore Size Ditribution Analysis of Gel Substances by Size Exclusion Chromatography" J. Chromatography, 206 (1981) 449-461.

(56) References Cited

OTHER PUBLICATIONS

Lin, Shan-Yang et al. "Influence of Excipients, Drugs, and Osmotic Agent in the Inner Core on the Time-Controlled Disintegration of Compression-Coated Ethylcellulose Tablets" Journal of Pharmaceutical Sciences, 91:9 (Sep. 2002) 2040-2046.

Maroni, Bradley J. et al. "Renal Bioreplacement Therapy is Associated with a Reduction in Mortality in Patients with Acute Renal Failure: Results of a Randomized, Multi-Center, Phase II Trial" ERA-EDTA: Abstract #551794 (2006).

Mattsson, S. et al. "Formulation of High Tensile Strength Rapidly Disintegrating Tablets Evaluation of the Effect of Some Binder Properties" S.T.P. Pharma Sciences, 11:3 (2001) 211-220.

Mitchell, Karen et al. "The Influence of Additives on the Cloud Point, Disintegration and Dissolution of Hydroxypropylmethylcellulose Gels and Matrix Tablets" International Journal of Pharmaceutics, 66 (1990) 233-242.

Mourey, T. H., et al., "Unique Behavior of Dendritic Molecules: Intrinsic Viscosity of Polyether Dendrimers" Macromolecules, 25 (1992) 2401-2406.

Newkome, George R. et al., "Improved Synthesis of an Ethereal Tetraamine Core for Dendrimer Construction" J. Org. Chem., 67 (2002) 3957-3960.

Pavlov, G. M. et al. "Molecular Characteristics of Poly(propylene imine) Dendrimers as Studied with Translational Diffusion and Viscometry" Colloid. Polym. Sci., 280 (2002) 416-423.

Pérignon, Nelly et al., "Formation and Stabilization in Water of Metal Nanoparticles by a Hyperbranched Polymer Chemically Analgous to PAMAM Dendrimers " Chem Mater., 16 (2004) 4856-4858.

"Renvela: sevelamer carbonate" Prescribing Information, Genzyme Corporation, Nov. 2007.

Rosenbaum, D.P, et al., "Effect of RenaGel, a non-absorbable, cross-linked, polymeric phosphate binder, on urinary phosphorus excretion in rats" Nephrology Dialysis Transplantation, vol. 12 (1997) 961-964.

Sarker, Dipak K. et al. "Restoration of Protein Foam Stability Through Electrostatic Propylene Glycol Alginate-Mediated Protein—Protein Interactions," Colloids and Surfaces B: Biointerfaces, 15 (1999) 203-213.

Schatzlein, Andreas G. et al., "Preferential liver gene expression with polypropylenimine dendrimers" Journal of Controlled Release, 101 (2005) 247-258.

Schulz, W. "Brief Evaluation: Sevelamer Hydrochloride" Drug, Therapy Criticism, Hans Marseille Publishers GmbH, Munich, Issue 3 (2001) 621-626.

Selmeczi, B. et al. "Investigations of the Influence of Some Novel Auxiliary Agents on the Physical Properties of Tablets" Pharmaceutical Technological Institute of the Medical University of Szeged (Hungary), [No date available].

Shao, Lu et al., "Transport properties of cross-linked polyimide membranes induced by different generations of diaminobutane (DAB) dendrimers" Journal of Membrane Science, 238 (2004) 153-163.

Soltero, Richard et al. "The Effects of PH. Ionic Concentration and Ionic Species of Dissolution Media on the Release Rates of Quinidine Gluconate Sustained Release Dosage Forms" Drug Development and Industrial Pharmacy, 17:1 (1991) 113-140.

Stasko, Nathan A. et al. "Dendrimers as a Scaffold for Nitric Oxide Release" J. Am. Chem. Soc., 128 (2006) 8265-8271.

Tirkkonen, Sirpa et al. "Enhancement of Drug Release from Ethylcellulose Microcapsules Using Solid Sodium Chloride in the Wall" International Journal of Pharmaceutics, 88 (1992) 39-51.

Tirkkonen, Sirpa et al. "Release of Indomethacin from Tabletted Ethylcellulose Microcapsules" International Journal of Pharmaceutics, 92 (1993) 55-62.

Ullmanns Encyklopadie der technischen Chemie—Band 19: Polyolefine (1980) pp. 167-178.

Xiao, Youchang et al., "Effects of Thermal Treatments and Dendrimers Chemical Structures on the Properties of Highly Surface Cross-Linked Polyimide Films" Ind. Eng. Chem. Res., 44 (2005) 3059-3067.

Xiuru Li, et al., "Synthesis and Characterization of Hyperbranched Poly(ester amide)s from Commercially Available Dicarboxylic Acids and Multihydroxyl Primary Amines", Macromolecules, 39 (2006) 7889-7899.

Yan, Deyue, "Hyperbranched Polymers Made from A2 and BB'2 Type Monomers. 1. Polyaddition of 1-(2-Aminoethyl)piperazine to Divinyl Sulfone" Macromolecules (2000), 33(21), 7693-7699.

Zabutaya, F.I., et al .. "Proton NMR spectroscopic study of the reaction of epichlorahydrin with allyamine," Uzb. Chinn. Zh., vol. 3 (1984) pp. 23-27. (English Abstract, see XP 002025287).

McGraw-Hill Dictionary of Scientific and Technical Terms, Third Ed., The Nikkan Kogyo Shimbu, Ltd., 1997, p. 54.

International Search Report dated Apr. 27, 2006 for PCT/US2005/039366.

Written Opinion dated Apr. 27, 2006 for PCT/US2005/039366.

Burt, Helen, et al., "Ion-Exchange Resins as Potential Phosphate-Binding Agents for Renal Failure Patients: Effect of the Physiochemical Properties of Resins on Phosphate and Bile Salt Binding," Journal of Pharmaceutical Sciences, vol. 76, No. 5 (May 1987) pp. 379-383.

C and C, Product Catalog, Manesty B3B Rotary Tablet Presses (Product# manesty-b3b-16) downloaded online, Mar. 5, 2014.

Delmez, James A., et al., "Hyperphosphatemia: Its Consequences and Treatment in Patients with Chronic Renal Disease," American Journal of Kidney Diseases, vol. XIX, No. 4 (1992) pp. 303-317.

Emmett, Michael, et al., "Calcium Acetate Control of Serum Phosphorus in Hemodialysis Patients," American Journal of Kidney Diseases, vol. XVII, No. 5 (1991) pp. 544-550.

Examination Report dated Jan. 20, 2011 for corresponding Australian Application No. 2006292672.

Examination Report dated Sep. 29, 2010 for Brazilian Application No. PI 0015061-4.

Examination Report dated Nov. 8, 2010 for Japanese Application No. 2001-531357.

Examination Report dated Oct. 12, 2013 for corresponding Chinese Application No. CN 201210583520.0.

Ghosh, J.P., et al., "Preparation and Properties of a New Chelating Resin Containing 2-Nitroso-1-naphthol," Talanta, vol. 28 (1981) pp. 957-959.

International Search Report dated Apr. 12, 2007 for corresponding PCT/US2006/035370.

Mai, Martin L., et al., "Calcium acetate, an effective phosphorus binder in patients with renal failure," Kidney International, vol. 36 (1989) pp. 690-695.

McGary, T.J., et al., "Polycation as an Alternative Osmotic Agent and Phosphate Binder in Peritoneal Dialysis," Uremia Investigation, vol. 8, No. 2 (1984-85) pp. 79-84.

Munson, Paul L., "Studies on the Role of the Parathyroids in Calcium and Phosphorus Metabolism," Annals New York Academy of Sciences (Jun. 1993) pp. 776-795.

Petrariu, I., et al., "Hofmann degradation in quaternary basic ammonium polymers: I. Degradation of the linear and crosslined basic benzylic polyelectrolytes in alkaline media," Majer. Plast. (Bucharest), vol. 9, No. 9 (1972) pp. 467-472.

Physicians Desk Reference "Renagel".

Physicians' Desk Reference, Consult 1992 Supplements for Revisions—"Amphojel® Suspension Tablets", p. 2429.

Physicians' Desk Reference, Consult 1992 Supplements for Revisions—"Phoslo® Calcium Acetate Tablets".

Proceedings of the American Chemical Society Division of Polymeric Materials: Science and Engineering, Boston, Massachusetts, vol. 62 (1990) pp. 259-263.

Salusky, I.B., et al., "Aluminum Accumulation During Treatment with Aluminum Hydroxide and Dialysis in Children and Young Adults with Chronic Renal Disease," The New England Journal of Medicine, vol. 324, No. 8 (1991) pp. 527-531.

(56) References Cited

OTHER PUBLICATIONS

Sarker, Dipak K., et al.; Colloids and Surfaces B: Biointerfaces, "Restoration of Protein Foam Stability Through Electrostatic Propylene Glycol Alginate-Mediated Protein-Protein Interactions," 1999, 15(3-4):203-213.

Shkinev, V.M., et al., "Anion exchange extraction and enrichment from aqueous solutions by quaternary ammonium reagents," Solvent Extraction and Ion Exchange, vol. 7, No. 3 (1989) pp. 499-510.

Slatopolsky, Eduardo, et al., "Calcium Carbonate as a Phosphate Binder in Patients with Chronic Renal Failure Undergoing Dialysis," The New England Journal of Medicine, vol. 315, No. 3 (1986) pp. 157-161.

Sugimoto, H., et al.; Journal of Food Processing and Preservations, 1981, 5:83-93.

Warshawsky, A., "Ion Exchange and Sorption Processes in Hydrometallurgy", Critical Reports on Applied Chemistry, vol. 19: Chapter 4: Chelating Ion Exchangers, M. Streat & D. Naden (Eds.), John Wiley & Sons (1987) pp. 166-225.

Winston, Anthony and Kirchner, Darrell, "Hydroxamic Acid Polymers. Effect of Structure of the Selective Chelation of Iron in Water," Macromolecules, vol. 11, No. 3 (1978) pp. 597-603.

Winston, Anthony and McLaughline, Glenn R., "Hydroxamic Acid Polymers. II. Design of a Polymeric Chelating Agent for Iron," Journal of Polymer Science, vol. 14 (1976) pp. 2155-2165.

Zhuzhu, "New Drug to Decrease the Phosphorous in Blood—Sevelamer Hydrochloride", Chinese Pharmaceutical Journal, 1999, 34:7, 496-497 [English translation provided].

SACHET FORMULATION FOR AMINE POLYMERS

CROSS REFERENCE TO RELATED APPLICATION

This application is a divisional of U.S. application Ser. No. 11/519,982, filed Sep. 12, 2006, which claims the benefit of U.S. Provisional Application 60/717,200, filed Sep. 15, 2005. The foregoing related applications, in their entirety, are incorporated herein by reference.

BACKGROUND OF THE INVENTION

Aliphatic amine polymers are effective as phosphate binders and have been described for the treatment of various conditions (see U.S. Pat. Nos. 5,496,545 and 5,667,775). For example, sevelamer hydrochloride, a crosslinked poly(allylamine) polymer, is currently sold under the trademark of RENAGEL® for removing phosphate from patients. Aliphatic amine polymers have also been described for the treatment of hypercholoestrolemia (see U.S. Pat. Nos. 5,624,963 and 5,679,717 and PCT Publication Nos. WO98/29107 and WO99/22721). For example, colesevelam, an alkylated, crosslinked poly(allylamine), is currently sold under the trademark of WELCHOL® for reducing serum cholesterol.

However, as the above products are currently available only as tablets, certain patient groups may benefit from the availability of these products in other dosage forms.

SUMMARY OF THE INVENTION

The present invention provides for, inter alia, new compositions and formulations of aliphatic amine polymers. One such formulation is a powder formulation that can be mixed with water and administered orally as a drink (solution or suspension), while providing acceptable properties to the patient such as mouth feel and taste. Applicants have found that in such formulations, a pharmaceutically acceptable anionic stabilizer, when mixed with the aliphatic amine polymer, can provide acceptable mouth-feel of an aliphatic amine polymer. Based on this discovery, a novel powder formulation for aliphatic amine polymer or a pharmaceutically acceptable salt thereof, a container containing the powder formulation and a method of treating a subject having hyperphosphatemia with the powder formulation are disclosed herein.

In one embodiment, the present invention provides for a container containing a powder that comprises a pharmaceutically acceptable anionic stabilizer and an aliphatic amine polymer or a pharmaceutically acceptable salt thereof mixed with the anionic stabilizer. The powder is uncapsulated and free-flowing.

In another embodiment, the present invention is a powder formulation comprising a pharmaceutically acceptable anionic stabilizer and an aliphatic amine polymer or a pharmaceutically acceptable salt thereof mixed with the pharmaceutically acceptable anionic stabilizer. Preferably, the only pharmaceutically active ingredient in the powder is the aliphatic amine polymer.

The present invention also provides a method of treating a subject with hyperphosphatemia. The method comprises the step of orally administering to the subject the disclosed powder formulation.

DETAILED DESCRIPTION OF THE INVENTION

The disclosed powder formulation comprises an aliphatic amine polymer and a pharmaceutically acceptable anionic stabilizer formulated so as to provide an acceptable mouth-feel. The powder formulation is typically dissolved and/or suspended in an ingestible liquid such as water and therefore can be conveniently administered to a patient as a drink. The drink can be even more palatable with one or more sweeteners and/or flavorants. Such powder formulations may be conveniently packaged in a container, such as a sachet or tub. As used herein, the terms "powder" and "powder formulation" are used interchangeably.

The powder formulations of the present invention may further comprise flavorants, sweeteners, excipients, fillers, inert ingredients and the like.

As used herein, "a pharmaceutically acceptable anionic stabilizer" is a compound which comprises an acid functional group (e.g., a carboxylic acid, sulfonic acid, phosphonic acid and the like, or a pharmaceutically acceptable salt thereof), and may substantially improve the mouth-feel of aliphatic amine polymers. The acid functional group is optionally neutralized with one or more pharmaceutically acceptable organic or inorganic bases to form a pharmaceutically acceptable salt. When the pharmaceutically acceptable anionic stabilizer includes more than one acid functional group, the acid functional groups can be partially or completely neutralized. Optionally, some of the acid functional groups can be esterified to form an ester of the acid functional group. Examples of organic or inorganic bases are, as described below.

The pharmaceutically acceptable anionic stabilizer typically has a solubility in water of greater than 1 mg/ml and a pKa value less than 9. The pharmaceutically acceptable anionic stabilizer should not interfere with the therapeutic activity of the aliphatic amine polymers, and should not cause unacceptable side effects at the dosages which are being administered.

The molecular weight of the pharmaceutically acceptable anionic stabilizer is not critical in the present invention as long as it has the features described above. Typically, the molecular weight of the pharmaceutically acceptable anionic stabilizer is greater than 1000 daltons. When the molecular weight of the pharmaceutically acceptable anionic stabilizer is greater than 1000 daltons, the charge density of the pharmaceutically acceptable anionic stabilizer is typically equal to or greater than 1 every 1000 daltons.

The pharmaceutically acceptable anionic stabilizer may not be a "pharmaceutically active ingredient".

In one embodiment, the pharmaceutically acceptable anionic stabilizer is an anionic polymer, such as an anionic polypeptide (e.g., a protein), an anionic polysaccharide or a polymer of one or more anionic monomers. Examples of anionic polymers include polymers of mannuronic acid, guluronic acid, acrylic acid, methacrylic acid, glucuronic acid, glutamic acid or a combination thereof, and pharmaceutically acceptable salts thereof. Other examples of anionic polymers include cellulose, such as a carboxyalkyl cellulose or a pharmaceutically acceptable salt thereof. An anionic polymer can be a homopolymer or a copolymer of two of the anionic monomers described above. Alternatively, the anionic copolymer comprises one or more repeat units of the anionic monomers described above and one or more neutral comonomers which are preferably inert and non-toxic. Examples of suitable neutral comonomers which can be used with, for example, olefinic anionic monomers, include vinyl alcohol, acrylamide and vinylformamide. Specific examples of anionic polymers include alginate (e.g., sodium alginate, potassium alginate, calcium alginate, magnesium alginate, ammonium alginate, esters of alginate, etc.), carboxymethyl cellulose, poly lactic acid, poly glutamic acid, pectin, xanthan, carrageenan, furcellaran, gum arabic, karaya gum, gum ghatti, gum carob and gum tragacanth.

In a preferred embodiment, the anionic polymer is an alginate, more preferably an esterified alginate, such as a C2-C5-diol ester of alginate or a C3-C5-triol ester of alginate. As used herein, an "esterified alginate" means an alginic acid in which some of the carboxyl groups of the alginic acid are esterified. The remainder of the carboxylic acid groups are optionally neutralized (partially or completely) as pharmaceutically acceptable salts. For example, propylene glycol alginate is an ester of alginic acid in which some of the carboxyl groups are esterified with propylene glycol, and the remainder of the carboxylic acid groups are optionally neutralized (partially or completely) as pharmaceutically acceptable salts. More preferably, the anionic polymer is ethylene glycol alginate, propylene glycol alginate or glycerol alginate. Propylene glycol alginate is even more preferred.

As noted above, the anionic polymer can be used in the form of a pharmaceutically acceptable salt (completely or partially neutralized). As used herein, a "pharmaceutically acceptable salt" refers to a salt prepared from pharmaceutically acceptable acids or bases. For example, the anionic polymers that possess a sufficiently acidic functional group can react with any of a number of pharmaceutically acceptable organic or inorganic bases to form a salt. Examples of salts include alkali metal and alkali earth metals, such as sodium, calcium, magnesium and potassium; zinc; and ammonium salts. Mixed salts are also included. "Ammonium" can be represented as $NR'_4{}^+$ where R' is —H or substituted or unsubstituted, linear or cyclic, or saturated or unsaturated alkyl, aryl or araryl. Examples of the ammonium include $NH_4{}^+$ and $N(R')H_3{}^+$, $N(R')_2H_2{}^+$, $N(R')_3H^+$ and $N(R')_4{}^+$, where R' is C1-C10 alkyl or phenyl.

In another embodiment, the pharmaceutically acceptable anionic stabilizer is an anionic polypeptide, including a protein. Examples of anionic polypeptides include gelatin, casein digest, whey protein, soy protein and polyglutamic acid.

One or more pharmaceutically acceptable anionic stabilizers can be used in the present invention.

The powder formulations of the invention typically include the pharmaceutically acceptable anionic stabilizer and aliphatic amine polymer in a ratio of 0.005-99.9:1 by weight, such as 0.005-50:1, 0.005-10:1; 0.005-3:1, 0.005-1:1, 0.005-0.05:1, and 0.008-0.05:1.

Aliphatic amine polymers are characterized by a repeat unit that includes at least one amine group. Amine groups can be part of the polymer backbone (e.g., a polyalkyleneimine such as polyethyleneimine) or pendant from the polymer backbone (e.g., polyallylamine). Alternatively, both types of amine groups can exist within the same repeat unit and/or polymer. The word "amine," as used herein, includes primary, secondary and tertiary amines, as well as ammonium groups such as trialkylammonium.

An aliphatic amine polymer may be obtained by polymerizing an aliphatic amine monomer. An aliphatic amine is saturated or unsaturated, straight-chained, branched or cyclic non-aromatic hydrocarbon having an amino substituent and optionally one or more additional substituents. An aliphatic amine monomer is an aliphatic amine comprising a polymerizable group such as an olefin. Suitable aliphatic amine polymers are described in U.S. Pat. Nos. 5,487,888, 5,496,545, 5,607,669, 5,618,530, 5,624,963, 5,667,775, 5,679,717, 5,703,188, 5,702,696, 5,693,675, 5,900,475, 5,925,379, 6,083,497, 6,177,478, 6,083,495, 6,203,785, 6,423,754, 6,509,013, 6,605,270, 6,726,905, 6,733,780 and 6,858,203 and U.S. Published Applications Nos. 2002/0159968 A1 and 2003/0086898 A1, the contents of which are incorporated herein by reference in their entireties.

An aliphatic amine polymer may be a homopolymer or a copolymer of one or more amine-containing monomers or a copolymer of one or more amine-containing monomers in combination with one or more non-amine containing monomers, which are preferably inert and non-toxic. Examples of suitable non-amine-containing monomers include vinyl alcohol, acrylic acid, acrylamide, and vinylformamide.

Examples of aliphatic amine polymers include polymers that have one or more repeat units selected from Formulas (1)-(6):

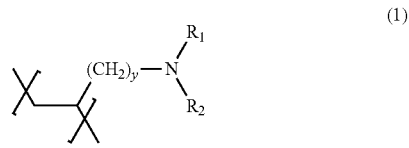

(1)

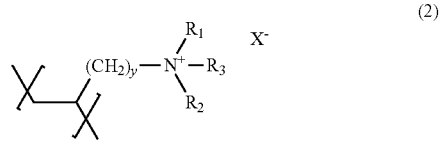

(2)

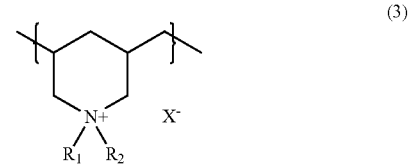

(3)

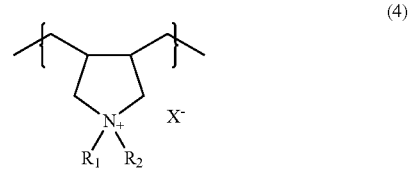

(4)

(5)

(6)

or a salt or copolymer thereof, where y is zero or an integer of one or more (e.g., between about one and about 10, preferably between one and four, more preferably one) and each R, $R_1$, $R_2$, and $R_3$, independently, is H, a substituted or unsubstituted alkyl group (e.g., having between 1 and 25 or between 1 and 5 carbon atoms, inclusive) or aryl (e.g., phenyl) group, and each $X^-$ is an exchangeable negatively charged counterion.

Preferably, at least one of R, $R_1$, $R_2$, or $R_3$ is a hydrogen atom. More preferably, each of these groups is hydrogen.

The alkyl or aryl group, represented by R, $R_1$, $R_2$, and $R_3$, can carry one or more substituents. Suitable substituents include cationic groups, e.g., quaternary ammonium groups, or amine groups, e.g., primary, secondary or tertiary alkyl or aryl amines. Examples of other suitable substituents include hydroxy, alkoxy, carboxamide, sulfonamide, halogen, alkyl, aryl, hydrazine, guanidine, urea, poly(alkyleneimine) such as poly(ethylenimine), and carboxylic acid esters.

Preferably, an aliphatic amine polymer is a homopolymer, such as a homopolyallylamine, homopolyvinylamine, homopolydiallylamine or polyethyleneamine.

In one embodiment, the aliphatic amine polymer is a homopolymer or copolymer characterized by one or more repeat units of Structural Formula (7):

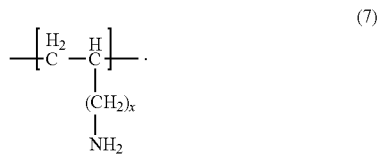

(7)

or a pharmaceutically acceptable salt thereof, where x is 0 or an integer between 1 and 4, preferably 1. The polymer represented by Structural Formula (7) is advantageously crosslinked by means of a cross-linking agent.

A preferred aliphatic amine polymer for use in the invention is polyallylamine, which is a polymer having repeat units from polymerized allyl amine monomers. The amine group of an allyl monomer can be unsubstituted or substituted with, for example, one or two C1-C10 straight chain or branched alkyl groups. These alkyl groups are optionally substituted with one or more hydroxyl, amine, halo, phenyl, amide or nitrile groups. Preferably, the aliphatic amine polymers of present invention are polyallylamine polymers comprising repeat units represented by Structural Formula (8):

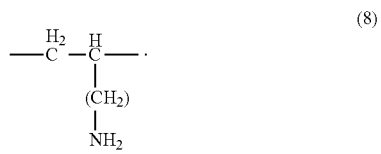

(8)

Polyallylamines that may be used as the aliphatic amine polymers of the present invention may include copolymers comprising repeat units from two or more different polymerized allyl monomers or with repeat units from one or more polymerized allyl monomers and repeat units from one or more polymerized non-allyl monomers. Examples of suitable non-allyl monomers include acrylamide monomers, acrylate monomers, maleic acid, malimide monomers, vinyl acylate monomers and alkyl substituted olefines. Preferably, however, the polyallylamines used in the present invention comprise repeat units solely from polymerized allyl amine monomers. More preferably, the polyallylamine polymers used in the present invention are homopolymers. Even more preferably, the polyallylamine polymers used in the present invention are homopolymers of repeat units represented by Structural Formula (8). Polyallylamine polymers used in the disclosed invention are preferably crosslinked polymers, more preferably crosslinked homopolymers.

In other embodiments, the aliphatic amine polymer can be a homopolymer or copolymer of polybutenylamine, polylysine, or polyarginine.

Preferably, the aliphatic amine polymer is rendered water-insoluble by cross-linking such as with a cross-linking agent. Suitable cross-linking agents include those with functional groups which react with the amino group of the aliphatic amine monomer. Alternatively, the cross-linking agent may contain two or more vinyl groups which undergo free radical polymerization with the amine monomer. In some cases the aliphatic amine polymers are crosslinked after polymerization.

Aliphatic amine polymers are typically crosslinked with difunctional cross-linking agents. Examples of suitable cross-linking agents include diacrylates and dimethylacrylates (e.g., ethylene glycol diacrylate, propylene glycol diacrylate, butylene glycol diacrylate, ethylene glycol dimethacrylate, propylene glycol dimethacrylate, butylene glycol dimethacrylate, polyethyleneglycol dimethacrylate and polyethyleneglycol diacrylate), methylene bisacrylamide, methylene bismethacrylamide, ethylene bisacrylamide, ethylene bismethacrylamide, ethylidene bisacrylamide, divinylbenzene, bisphenol A, the diglycidal ether of bisphenol A, pyromellitic dianhydride, toluene diisocyanate, ethylene diamine and dimethyl succinate, dimethacrylate, and bisphenol A diacrylate. Examples of preferred difunctional crosslinking agents include epichlorohydrin, 1,4 butanediol-diglycidyl ether, 1,2 ethanedioldiglycidyl ether, 1,3-dichloropropane, 1,2-dichloroethane, 1,3-dibromopropane, 1,2-dibromoethane, succinyl dichloride, dimethylsuccinate, toluene diisocyanate, acryloyl chloride, and pyromellitic dianhydride. Epichlorohydrin is a most preferred crosslinking agent, because of its high availability and low cost. Epichlorohydrin is also advantageous because of its low molecular weight and hydrophilic nature, increasing the water-swellability and gel properties of the polyamine. Epichlorohydrin forms 2-hydroxypropyl crosslinking groups.

Other methods of inducing crosslinking on already polymerized materials include, but are not limited to, exposure to ionizing radiation, ultraviolet radiation, electron beams, radicals, and pyrolysis.

The level of cross-linking renders the aliphatic amine polymers insoluble and substantially resistant to absorption and degradation, thereby limiting the activity of the aliphatic amine polymer to the gastrointestinal tract, and reducing potential side-effects in the patient. Typically, the cross-linking agent is present in an amount from about 0.5-35% or about 0.5-25% (such as from about 2.5-20% or about 1-10%) by weight, based upon total weight of aliphatic amine monomer plus cross-linking agent. Typically, the amount of cross-linking agent is measured as a percentage of the combined weight of aliphatic amine polymer and cross-linking agent.

Typically, between about 9% and about 30% of the allylic nitrogen atoms are bonded to a crosslinking group, preferably between 15% and about 21%.

The aliphatic amine polymers can also be further derivatized; examples include alkylated amine polymers, as described, for example, in U.S. Pat. Nos. 5,679,717, 5,607,669 and 5,618,530, the teachings of which are incorporated herein by reference in their entireties. Preferred alkylating agents include hydrophobic groups (such as aliphatic hydrophobic groups) and/or quaternary ammonium- or amine-substituted alkyl groups.

Non-cross-linked and cross-linked polyallylamine and polyvinylamine are generally known in the art and are commercially available. Methods for the manufacture of polyallylamine and polyvinyl amine, and cross-linked derivatives thereof, are described in the above U.S. Patents. Patents by Harada et al., (U.S. Pat. Nos. 4,605,701 and 4,528,347), which are incorporated herein by reference in their entireties, also describe methods of manufacturing polyallylamine and cross-linked polyallylamine. A patent by Stutts et al., (U.S. Pat. No. 6,180,754) describes an additional method of manufacturing cross-linked polyallylamine.

The molecular weight of aliphatic amine polymers is not believed to be critical, provided that the molecular weight is large enough so that the aliphatic amine polymer is non-absorbable by the gastrointestinal tract. Typically, the molecular weight of aliphatic amine polymers is at least 1000. For example the molecular weight can be from: about 1000 to about 5 million, about 1000 to about 3 million, about 1000 to about 2 million or about 1000 to about 1 million.

The aliphatic amine polymers used in the invention may be optionally protonated, and in one embodiment, include polymers in which less than 40%, for example, less than 30%, such as less than 20% or less than 10% of the amine groups are protonated. In another embodiment 35% to 45% of the amines are protonated (e.g., approximately 40%). An example of a suitably protonated aliphatic amine polymer is sevelamer.

As described above, the aliphatic amine polymer can be administered in the form of a pharmaceutically acceptable salt. The term "pharmaceutically acceptable salt" refers to a salt of the aliphatic amine polymer to be administered prepared from pharmaceutically acceptable non-toxic acids including inorganic acids, organic acids, solvates, hydrates, or clathrates thereof. Thus, the nitrogen group in the repeat unit of the aliphatic amine polymer is protonated to create a positively charged nitrogen atom associated with a negatively charged counterion.

Examples of suitable counterions include organic ions, inorganic ions, or a combination thereof. For instance, suitable counterions include halides (e.g., $F^-$, $Cl^-$, $Br^-$ and $I^-$), $CH_3OSO_3^-$, $HSO_4^-$, $SO_4^{2-}$, $HCO_3^-$, $CO_3^{2-}$, acetate, lactate, succinate, propionate, oxalate, butyrate, ascorbate, citrate, dihydrogen citrate, tartrate, taurocholate, glycocholate, cholate, hydrogen citrate, maleate, benzoate, folate, an amino acid derivative, a nucleotide, a lipid, or a phospholipid. Preferred anions are $Cl^-$, $HCO_3^-$, $CO_3^{2-}$, and a combination thereof (e.g., a mixed carbonate and bicarbonate salt, a mixed carbonate and chloride salt, or a mixed bicarbonate and chloride salt). The counterions can be the same as, or different from, each other. For example, the polymer can contain two or more different types of counterions.

In a preferred embodiment, the aliphatic amine polymer used in the present invention is an epichlorohydrin cross-linked polyallylamine, such as sevelamer and colesevelam (see, for example, U.S. Pat. Nos. 6,423,754; 5,607,669; and 5,679,717, the contents of which are incorporated herein by reference). In a preferred embodiment, the polyallylamine polymer is crosslinked with epichlorohydrin and between about 9% to about 30% (preferably about 15% to about 21%) of the allylic nitrogen atoms are bonded to a cross-linking group and the anion is chloride, carbonate or bicarbonate or a mixed salt thereof.

A particularly preferred aliphatic mine polymer is polyallylamine hydrochloride crosslinked with about 9.0-9.8% w/w epichlorohydrin, preferably 9.3-9.5%, and is the active chemical component of the drug known as sevelamer HCl, sold under the tradename RENAGEL®. The structure is represented below:

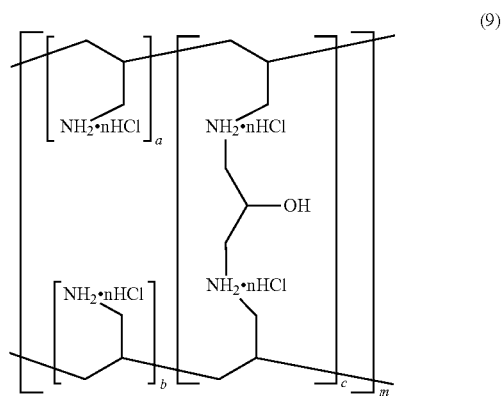

where:
the sum of a and b (the number of primary amine groups) is 9;
c (the number of crosslinking groups) is 1;
n (the fraction of protonated amines) is 0.4; and
m is a large number (to indicate extended polymer network).

Another particularly preferred aliphatic amine polymer is polyallylamine hydrochloride crosslinked with epichlorohydrin and alkyated with 1-bromodecane and (6-bromohexyl)-trimethylammonium bromide, referred to as colesevelam HCl, and marketed in the United States as WELCHOL®.

In yet another particularly preferred embodiment, the aliphatic amine polymer is a carbonate salt of sevelamer; a bicarbonate salt of sevelamer; a mixed carbonate and bicarbonate salt of sevelamer; or a mixed carbonate and chloride salt of sevelamer.

In other embodiments, a monovalent anionic source is mixed with a carbonate salt of the aliphatic amine polymer. Various examples of carbonate salts of the aliphatic amine polymer and monovalent anionic sources are disclosed in U.S. Provisional Application No. 60/624,001 "Aliphatic Amine Polymer Salts For Tableting" filed Nov. 1, 2004 and U.S. Provisional Application No. 60/628,752 "Aliphatic Amine Polymer Salts For Tableting" filed Nov. 17, 2004, the entire contents of which are incorporated herein by reference.

The monovalent anion comprises at least 0.01%, preferably 0.05%, more preferably a range of 0.01% to 2%, 0.05% to 1%, 0.08% to 0.5%, or 0.1% to 0.3% by weight of the combined weights of the carbonate salt of aliphatic amine polymer and the monovalent anion source.

Examples of suitable monovalent anions include organic ions, inorganic ions, or a combination thereof, such as halides ($Cl^-$, $I^-$, $Fl^-$, and $Br^-$), $CH_3OSO_3^-$, $HSO_4^-$, acetate, lactate, butyrate, propionate, sulphate, citrate, tartrate, nitrate, sulfonate, oxalate, succinate or palmoate. Preferred monovalent anions are halides, most preferably chloride.

Also, the monovalent anion source can be a pharmaceutically acceptable acid, ammonium or metal salt of a monovalent anion. Preferably the monovalent anion source is sodium chloride or hydrochloric acid. In one preferred embodiment, the formulations of the invention comprise a carbonate salt of sevelamer and sodium chloride. In another preferred embodiment, the formulations of the invention comprise a carbonate salt of sevelamer and hydrochloric acid.

In yet another preferred embodiment, the monovalent anion source can be a monovalent anion salt of an aliphatic amine polymer comprising a repeat unit represented by Structural Formulas (1)-(8) above. The formulations of the invention can comprise a "physically mixed polymer" or a "chemically mixed polymer". The combination of a carbonate salt of an aliphatic amine polymer and a monovalent anion salt of an aliphatic amine polymer is defined herein as a "physically mixed polymer". The monovalent anion salt of the aliphatic amine polymer can be the same or a different aliphatic amine polymer as the aliphatic amine polymer carbonate salt. Herein, a "chemically mixed polymer" means the combination of a carbonate salt and a monovalent anion salt on a single aliphatic amine polymer.

In some embodiments, the aliphatic amine polymer or pharmaceutically acceptable salt thereof is the only pharmaceutically active ingredient in the powder formulations.

The powder formulations of the invention for use in a subject comprise the aliphatic amine polymer and the pharmaceutically acceptable anionic stabilizer(s), optionally together with one or more acceptable excipients therefor. The excipients include carriers or diluents, such as lactose, starch, cellulose and dextrose; flavoring agents; sweeteners; and preservatives, such as methyl, ethyl, propyl and butyl parabens. Optionally, for a good appearance, excipients, such as microcrystalline cellulose, titanium dioxide, and/or coloring agents, such as FD&C Blue #1, FD&C Red #40, D&C Yellow #10, D&C Red #33, or yellow iron oxide, can also be included in the powder formulations of the invention. Examples of suitable sweeteners include sucrose; glucose (corn syrup); dextrose; invert sugar; fructose; saccharin and its various salts, such as sodium saccharinate; sodium, aspartame, xylose; maltitol; maltol; potassium acesulfame; neohesperidin dihydrochalcone; monoammonium glycyrrhizinate; maltodextrin and polydextrose saccharin and its various salts such as the sodium and calcium salts; cyclamic acid and its various salts; dipeptide sweeteners; sucralose; dihydrochalcone; glycyrrhin; *Stevia rebaudiana* (Stevioside); sorbitol; mannitol; xylitol; hexa-resorcinol; hydrogenated starch hydrolysate (lycasin), and the potassium, calcium and sodium salts of 3,6-dihydro-6-methyl-1-1,2,3-oxathiazin-4-on 3-2,2-dioxide, and a mixture of thereof. Of the foregoing, sucralose, sucrose, xylose, mannitol, maltitol, maltol, sorbitol or xylitol is particularly preferred, either alone or more desirably in combination. Suitable flavorings include grape, cherry, peppermint, menthol and vanilla flavors, such as orange vanilla flavor, lemon flavor, spearmint, wintergreen, cinnamon, menthone flavors, or a mixture thereof. The excipients must be "acceptable" in the sense of being compatible with the other ingredients of the formulation and not deleterious to the recipient thereof.

Typically, the average particle size of the powder of the invention is less than 500 microns, preferably less than 200 microns. In some embodiments, the powder contains less than 5 wt %, preferably less than 2 wt %, more preferably less than 1 wt %, of particles having a particle size more than 300 microns and less than 5 wt %, preferably less than 2 wt %, more preferably less than 1 wt %, of particles having a particle size less than 10 microns.

The disclosed powder formulation is typically dissolved and/or suspended in an ingestible liquid such as water. The resulting mixture has a pleasant mouth-feel and therefore can be conveniently administered to a patient as a drink. The drink can be a suspension or solution. The drink can be even more palatable with one or more sweeteners and/or flavorants. Alternatively, the disclosed powder formulation can be mixed with foods, such as mashed potatoes or oatmeal.

The powder formulations of the invention can be conveniently packaged in a container. Herein, a "container" is a non-ingestible containment device which can hold and preserve the stability of the powder formulation of the invention for a sufficient period of time, i.e., from the time of manufacture to the time of consumption by patients. As noted above, the powder formulation is uncapsulated and free-flowing. Containers suitable for the present invention include a sachet, such as a paper bag, powder bag of plastic films or metal foils; a bottle, such as a glass, plastic or metal bottle; a tub; and an ampule. Preferably, the container of the invention is a sachet. The container material is preferably impermeable to water and water vapor in order that the stability of the active agent contained in the container is ensured. Optionally, the container materials can contain substances which impart a particular type of protection, for example protection against light, to the contents. Examples of suitable container materials include plastics, such as MATT LACQUER/PET 23µ/PX 12GR/AL 12µ/SURLYN 23GR (AMCOR Flexibles in Victoria, Australia), coated papers, such as Coated Paper 40GR/PX 12 GR/AL 12µ/SURLYN 23 GR (AMCOR Flexibles in Victoria, Australia), foil pouches, such as TPC-2475 (TOLAS Health Care Packaging in Feasterville, Pa.), and a combination of these materials (e.g., laminates).

Preferably, the container is a multi-layer container having multiple layers of different container materials discussed above.

The container containing the powder formulation of the invention can be a unit-dose or a multi-dose container. For example, the container of the invention can contain a single dose of the aliphatic amine polymer mixed with the pharmaceutically acceptable anionic stabilizer, such as a single-dose sachet. Alternatively, the container of the invention can contain at least two doses of the aliphatic amine polymer mixed with the pharmaceutically acceptable anionic stabilizer, such as a bottle or tub with the powder formulation from which a unit dose is measured by, e.g., a spoon or cup, or an instrument capable of dispensing a pre-defined dosage amount. Herein, a "tub" means a container containing a bulk quantity of the powder formulation. A "bulk quantity" means an amount out of which a plurality of unit doses can be divided, e.g., 2, 10, 50, 100 or more unit doses.

The powder formulations of the invention can be prepared by any of the methods known in the art of pharmacy. For example, standard pharmaceutical formulation techniques such as those described in Remington's Pharmaceutical Sciences, 18th ed. (1990), Mack Publishing Company, Easton, Pa., the disclosure of which is incorporated herein by reference, can be used. Typically, the methods include the steps of mixing at least one aliphatic amine polymer with one or more pharmaceutically acceptable anionic stabilizers, and bringing into association the resulting mixture with any additional excipients. In general, the formulations are prepared by uniformly and intimately bringing the aliphatic amine polymer into association with the pharmaceutically acceptable anionic stabilizers and then, if necessary, dividing the product into unit dosages thereof. The powder formulation is then packaged within a suitable container, such as a sachet.

Typically, the container holds a unit dose which is generally about 5 mg to about 15 g (e.g., 600 mg-7.5 g, 600 mg-5 g, 800 mg-3.5 g and 800 mg-2.5 g) of the aliphatic amine polymer on an anhydrous basis if administered once a day. Typically, about 0.025 mg to about to about 14.9 g (e.g., 3 mg-7.5 g; 3 mg-5 g; 8 mg-3.5 g; 8 mg-2.5 g; 6 mg-2.5 g, 6 mg-1.5 g, 6 mg-0.75 g) of a pharmaceutically acceptable anionic stabilizer is included in the unit dose together with the aliphatic amine polymer. Alternatively, the container holds a unit dose which is generally the daily dosage divided by the number of administration per day if administered multiple times per day (e.g., 2, 3, 4, or 5 times/day). In one example, a sachet contains either 800 mg, 1.6 g, 2.4 g, 3.2 g, 4.0 g, 4.8 g, 5.6 g, 7.2 g or 9.6 g of sevelamer on an anhydrous basis, and further contains propylene glycol alginate and optional excipients, such as sucrose, xylose, mannitol, maltitol, maltol, sodium chloride, yellow iron oxide, orange vanilla flavor and lemon flavor mixed with sevelamer.

The powder formulation may be introduced by a patient into a suitable amount of liquid, preferably water, to form a therapeutic formulation in situ, and the therapeutic formulation is then taken by the patient. The therapeutic formulation can be an aqueous-based therapeutic formulation or a non-aqueous formulation, preferably aqueous-based formulation, in which the aliphatic amine polymer and anionic stabilizer are each independently dissolved or suspended. Aqueous-based therapeutic formulations can be formed by adding the powder formulation within a container into a suitable aqueous vehicle, such as water, before administration. Non-aqueous therapeutic formulations can be obtained by dispersing in a suitable non-aqueous based vehicle, such as almond oil, arachis oil, soybean oil, fractionated coconut oil, olive oil, poppy-seed oil or maize oil before administration. Alternatively, the powder formulations of the invention may be administered by a patient via direct ingestion. That is, a unit dose of the powder is administered directly into a mouth of the patient and then swallowed, preferably with the aid of water or any other ingestible liquid. Optionally, the powder formulations of the invention may be administered by a patient as a mixture with foods.

The powder formulations of the invention can be used for treating hyperphospatemia in a subject. Hyperphosphatemia is typically defined for humans as a serum phosphate level of greater than about 4.5 mg/dL. The condition, especially if present over extended periods of time, leads to severe abnormalities in calcium and phosphorus metabolism and can be manifested by aberrant calcification in joints, lungs and eyes. Elevated serum phosphate is commonly present in patients with renal insufficiency, hypoparathyroidism, pseudohypoparathyroidism, acute untreated acromegaly, overmedication with phosphate salts, and acute tissue destruction as occurs during rhabdomyolysis and treatment of malignancies.

As used herein a subject is a mammal, preferably a human, but can also be an animal in need of veterinary treatment, such as a companion animal (e.g., dogs, cats, and the like), a farm animal (e.g., cows, sheep, pigs, horses, and the like) or a laboratory animal (e.g., rats, mice, guinea pigs, and the like). A subject "in need of treatment" includes a subject with chronic renal failure. Other examples of subjects in need of treatment include patients with a disease associated with disorders of phosphate metabolism. Examples of diseases and/or disorders of this type include hyperparathyroidism, inadequate renal function, and hyperphosphatemia.

An "effective amount" of an aliphatic amine polymer is a quantity that results in a beneficial clinical outcome of or exerts an influence on, the condition being treated with the aliphatic amine polymer compared with the absence of treatment. The amount of an aliphatic amine polymer administered to the subject will depend on the degree, severity, and type of the disease or condition, the amount of therapy desired, and the release characteristics of the pharmaceutical formulation. It will also depend on the subject's health, size, weight, age, sex and tolerance to drugs. Typically, the composition of the invention is administered for a sufficient period of time to achieve the desired therapeutic effect. Typically between about 5 mg per day and about 15 g per day of an aliphatic amine polymer (alternatively between about 50 mg per day and about 10 g per day, alternatively between about 1 g per day and about 10 g per day, alternatively between about 1 g per day and about 8 g per day, alternatively between about 2 g per day and about 8 g per day, alternatively between about 4 g per day and about 8 g per day) is administered to the subject in need of treatment. These dosages can be administered, several times/day (e.g., 2, 3, 4 or 5 times/day) or once/day. The aliphatic amine polymer can be administered at least four times per day with meals, at least three times per day with meals, at least twice per day with meals, at least once per day with meals, (see U.S. Provisional Application No. 60/623,985, "Once a day formulation for phosphate binders" filed Nov. 1, 2004, the entire contents of which are incorporated herein by reference). In one specific example, about 0.8-7.2 g (e.g., 2.4 g or 3.2 g per dose for 2-3 times per day, or 4.0 or 4.8 g per dose for 2-3 times per day, or 7.2 g per dose for once per day) of the aliphatic amine polymer is administered per day.

Typically, the formulations of the invention can be administered before or after a meal, or with a meal. As used herein, "before" or "after" a meal is typically within two hours, preferably within one hour, more preferably within thirty minutes, most preferably within ten minutes of commencing or finishing a meal, respectively.

The method of the present invention includes a monotherapy where the powder formulations of the invention are used alone. The method of the present invention also includes a co-therapy with other therapeutically active drugs. For example, the method of the present invention can be used with other phosphate binders including pharmaceutically acceptable lanthanum, calcium, aluminum and iron salts, such as acetates, carbonates, oxides, hydroxides, citrates, alginates, and ketoacids. Calcium salts, including calcium carbonate, acetate (such as PhosLo® calcium acetate tablets), citrate, alginate, and ketoacids, have been utilized for phosphate binding. The ingested calcium combines with phosphate to form insoluble calcium phosphate salts such as $Ca_3(PO_4)_2$, $CaHPO_4$, or $Ca(H_2PO_4)_2$. Aluminium-based phosphate binders, such as Amphojel® aluminium hydroxide gel, have also been used for treating hyperphosphatemia. These compounds complex with intestinal phosphate to form highly insoluble aluminium phosphate; the bound phosphate is unavailable for absorption by the patient. More recently iron and lanthanide salts have been used. The most commonly used lanthanide salt, lanthanum carbonate (Fosrenol®) behaves similarly to calcium carbonate.

Those skilled in the art will be aware that the amounts of the various components of the formulations of the invention to be administered in accordance with the method of the invention to a subject will depend upon those factors noted above.

The invention is illustrated by the following examples which are not intended to be limiting in any way.

EXEMPLIFICATION

Example 1

Compositions of Powder Formulations of the Invention

The powder formulations were prepared by standard pharmaceutical formulation techniques such as those described in Remington's Pharmaceutical Sciences, 18th ed. (1990), Mack Publishing Company, Easton, Pa. Specific compositions of two exemplary powder formulations (Formulas A and B) of the invention are summarized in Table 1 below:

TABLE 1

Compositions of the Powder Formulations

| Ingredients | Formula A (wt %) | Formula B (wt %) |
|---|---|---|
| Anhydrous Sevelamer HCl | | 92.90 |
| Anhydrous Sevelamer carbonate | 94.97 | |
| PGA | 1.00 | 3.00 |
| Orange Vanilla PR90 | 2.00 | 2.00 |
| WG55 Vanilla | 0.50 | 0.50 |
| Lemon Lime | 0.11 | 0.12 |
| NaCl | 1.00 | 1.00 |
| Sucralose | 0.40 | 0.45 |
| Yellow iron oxide | 0.016 | 0.016 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a patient suffering from hyperphatemia, comprising:
    administering to the patient a therapeutically effective amount of powder formulation comprising a mixture of:
    a) a pharmaceutically acceptable anionic stabilizer comprising an esterified alginate;
    b) carbonate salt of sevelamer mixed with the anionic stabilizer; and
    c) sodium chloride;
    wherein:
    i) the ratio of the anionic stabilizer to sevelamer carbonate is 0.005-1:1; and
    ii) the only pharmaceutically active ingredient in the powder is the sevelamer carbonate.
2. The method of treating of claim 1, wherein the esterified alginate is a propylene glycol alginate.
3. The method of treating of claim 1, wherein the amount of the sevelamer carbonate is 800 mg on an anhydrous basis.
4. The method of treating of claim 1, wherein the amount of the sevelamer carbonate is 2.4 g on an anhydrous basis.
5. The method of treating of claim 1, wherein the chloride of the sodium chloride is present in a range of between 0.01-2 wt. % relative to the combined weights of the sevelamer carbonate and the sodium chloride.
6. The method of treating of claim 1, wherein the chloride of the sodium chloride is present in a range of between 0.05-1 wt. % relative to the combined weights of the sevelamer carbonate and the sodium chloride.
7. The method of treating of claim 1, wherein the chloride of the sodium chloride is present in a range of between 0.08-0.5 wt. % relative to the combined weights of the sevelamer carbonate and the sodium chloride.
8. The method of treating of claim 1, wherein the powder is uncapsulated and free-flowing, and wherein the powder contains less than 5 wt % of particles having a particle size more than 300 microns and less than 5 wt % of particles having a particle size less than 10 microns.
9. The method of treating of claim 1, wherein the powder formulation further comprises one or more of a pharmaceutically acceptable flavoring agent, sweetener, or coloring agent.
10. The method of treating of claim 9, wherein the powder formulation further comprises a pharmaceutically acceptable flavoring agent.
11. The method of treating of claim 10, wherein the pharmaceutically acceptable flavoring agent includes at least one member selected from the group consisting of grape, cherry, peppermint, menthol, vanilla flavor, orange vanilla flavor, lemon flavor, spearmint, wintergreen, cinnamon, and menthone flavors.
12. The method of treating of claim 11, wherein the at least one pharmaceutically acceptable flavoring agent is lemon flavor.
13. The method of treating of claim 9, wherein the powder formulation further comprises a pharmaceutically acceptable sweetener.
14. The method of treating of claim 13, wherein the pharmaceutically acceptable sweetener includes at least one member selected from the group consisting of sucralose, sucrose, xylose, mannitol, maltitol, maltol, sorbitol and xylitol.
15. The method of treating of claim 14, wherein the at least one pharmaceutically acceptable sweetener is sucralose.
16. The method of treating of claim 9, wherein the powder formulation further comprises a pharmaceutically acceptable coloring agent.
17. The method of treating of claim 16, wherein the pharmaceutically acceptable coloring agent is yellow iron oxide.
18. The method of treating of claim 1, wherein the subject has a serum phosphate level of greater than about 4.5 mg/dL.
19. The method of treating of claim 1, wherein the therapeutically effective amount of the powder formulation is orally administered to the patient.
20. The method of treating of claim 1, wherein the powder formulation is packaged in a unit-dose container or a multi-dose container.
21. The method of treating of claim 20, wherein the unit-dose container or multi-dose container is a tub or sachet.

* * * * *